United States Patent [19]

Bernal

[11] Patent Number: 4,585,742

[45] Date of Patent: Apr. 29, 1986

[54] MONOCLONAL ANTIBODY WITH SPECIFICITY TO HUMAN SMALL CELL CARCINOMA AND USE THEREOF

[75] Inventor: Samuel D. Bernal, Wellesley, Mass.

[73] Assignee: Dana-Farber Cancer Institute, Inc., Boston, Mass.

[21] Appl. No.: 561,196

[22] Filed: Dec. 14, 1983

[51] Int. Cl.[4] ................ G01N 53/00; G01N 33/44; G01N 33/53; G01N 33/48; G01N 33/564; C12N 15/00; A61K 39/00

[52] U.S. Cl. .................... 436/548; 435/68; 435/172.1; 435/240; 435/259; 436/64; 436/507; 436/545; 436/546; 436/813; 436/821; 260/112 B; 424/85

[58] Field of Search ............... 435/7, 68, 172.2, 178.1, 435/181, 240, 247, 948, 259; 260/112 R, 112 B; 424/85, 177; 436/821, 548, 546, 813, 834, 64, 68

[56] References Cited

PUBLICATIONS

Baylin et al., *Proc. Natl Acad. Sci.*, vol. 79, pp. 1650–1655, "A Unique Cell–Surface Protein Phenotype Distinguishes Human Small-Cell from Non-Small Cell Lung Cancer.

Mazauric et al., "Monoclonal Antibody–Defined Human Lung Living Cell Surface Protein Antigens", *Cancer Research*, V. 42, pp. 150–154, Jan. 1982.

Cuttitta et al., "Monoclonal Antibodies That Demonstrate Specificity For Several Types of Lung Cancer", *Proc. Nat'l. Acad. Sci.*, V. 78, No. 7, Jul. 1981, pp. 4591–4595.

*Primary Examiner*—Thomas G. Wiseman
*Assistant Examiner*—Robin Lyn Teskin

[57] ABSTRACT

Monoclonal antibody reactive with SCC cells and unreactive with human neuroblastoma cells, human squamous cell carcinoma cells, and human large-cell undifferentiated lung carcinoma cells.

15 Claims, No Drawings

MONOCLONAL ANTIBODY WITH SPECIFICITY TO HUMAN SMALL CELL CARCINOMA AND USE THEREOF

BACKGROUND OF THE INVENTION

This invention relates to monoclonal antibodies.

Cuttitta et al. (1981) Proc. Natl. Acad. Sci. 78 4591 describe monoclonal antibodies that react with human small cell carcinoma of the lung (SCC), adenocarcinoma, and squamous carcinoma, as well as with human neuroblastomas and breast cancer cells. Mazauric et al. (1982) Cancer Res. 42 150 describe monoclonal antibodies that react with several non-SCC lung cancer cells, colon carcinoma cells, breast carcinoma cells, and with melanoma cells.

SUMMARY OF THE INVENTION

In general, the invention features, in one aspect, a monoclonal antibody reactive with SCC cells and unreactive with human neuroblastoma cells, human squamous cell carcinoma cells, and human large-cell undifferentiated lung carcinoma cells.

In preferred embodiments the antibody is of the IgM or IgG2 isotype and recognizes an approximately 50,000 dalton antigenic determinant on the surface of SCC cells, or an approximately 25,000 dalton antigenic determinant on the surface of SCC cells, or both. The antibody is preferably capable of lysing SCC cells in vitro in the presence of complement.

The antibody of the invention can be labeled, e.g. with radioactive or fluorescent label, and used to identify SCC tumor cells and to distinguish these cells from non-cancerous cells and from non-SCC lung tumor cells. Furthermore, anti-SCC of the invention can be used therapeutically to treat patients suffering from SCC; the antibody can be administered to the patient alone or can be administered coupled to a cytotoxic agent. The antibody can also be used to cleanse a clinical sample, e.g. bone marrow, of metastatic SCC cells.

All monoclonal antibodies having the above characteristics and being specific for SCC cells are encompassed by the present invention. These monoclonal antibodies are produced by hybrid cells made using conventional hybridization and screening techniques such as are described in Reinherz et al. (1979) J. Immunol. 123, 1312 and Ritz et al. Nature (1980) 283, 583. As is well-known in the monoclonal antibody field, each independently-produced hybrid cell line which produces a monoclonal antibody specific to the same particular antigenic determinant is nonetheless different from all others, as is each of the monoclonal antibodies so produced. Thus, while repetition of the procedure described below can result in the production of a hybrid cell line which produces useful monoclonal antibody specific to SCC cells, it is highly unlikely that it will produce a cell line which produces a monoclonal antibody which is chemically an exact copy of the monoclonal antibody described below.

DESCRIPTION OF THE PREFERRED EMBODIMENTS

We now turn to a description of the preferred embodiments of the invention.

Production of SM1 Hybridoma

BALB/c mice are immunized by four weekly intraperitoneal injections of $10^7$ SCC cells, e.g., the SCC cell line designated OH-1, described in Francis et al. (1983) Cancer Res. 43 639–645. After a four week rest period, the mice are given injections of SCC cells 4 times at two day intervals. The spleen is removed three days after the last injection, and the spleen cells are fused with myeloma cells, e.g., the mouse cell line SP3-NS1-AG-4-1, at a ratio of 2 spleen cells/myeloma cell in 1 ml of 50% (u/v) polyethylene glycol for 1 min at 37° C. The cell suspension is then diluted with 8 milliliters of RPMI without serum for 2 min. The cells are pelleted by centrifugation and resuspended in RPMI with 10% calf serum. The cells are distributed to 96-well microtiter plates at $1 \times 10^5$ cells/well. Starting at 24 hr. after cell fusion, the plates are fed with RPMI containing HAT medium. More HAT medium is added on Days 3 and 7 after fusion. On Day 10, the medium is replaced with RPMI containing hypoxanthine and thymidine but no aminopterin. At the end of the second week 60% of the wells are found to contain growing hybridoma cells. One of these, designated SM1, is highly reactive with SCC. The cells are subcloned in methocel and screened for reactivity with SCC. Antibody production remains stable after freeze/thawing, serial passage in culture flasks, and propagation as ascites cells in Balb/C mice. SM1 cells have been deposited in the American Type Culture Collection, Rockville, Md., and are given ATCC Accession No. HB8462.

Characterization of SM1 Antibody

The isotype of SM1 antibody is determined by immunodiffusion and by indirect immunofluorescence. Immunodiffusion is performed on supernatant fluid from SM1 hybridoma culture and on SM1 ascites fluid using goat anti-mouse IgG1, IgG2, IgM, and IgA. SCC cells are incubated with SM1 ascites fluid and tested by indirect immunofluorescence for reactivity with fluoresceinconjugated goat anti-mouse IgG1, IgG2, and IgM (Cappel Laboratories, Downington, Pa.). Both techniques show SM1 antibody to be of the IgM isotype.

SM1's reactivity pattern is determined both by indirect immunofluorescence and by radioimmunoassay. Suspension cells, cells attached to coverslips, or frozen sections are prepared for indirect immunofluorescence by washing three times with RPMI without serum. Either 50 microliters of hybridoma supernatent or 50 microliters of ascites fluid diluted 1:1000 are applied to the test cells or tissues and incubated 30 min at 37° C. the specimens are washed three times with PBS and incubated for 30 min with fluorescein-conjugated goat anti-mouse IgG (Meloy Laboratories, Inc., Springfield, Va.) at 1:50 dilution with PBS. After three rinses with PBS, the cells are observed for fluorescence staining using a Zeiss epifluorescence microscope. MPR-1 (from Dr. E Yunis, Dana-Farber Cancer Institute), a mouse IgM monoclonal antibody, is used as a negative control antibody; another mouse monoclonal antibody (designated SM15) is used as a positive control antibody.

To prepare specimens for radioimmunoassays, suspension cell lines and cells scraped from tissue culture dishes are washed three times with RPMI without serum. Tumor and normal tissues are cut into small pieces with fine scissors and minced with a scalpel and forceps. The cell suspensions are then transferred to a centrifuge tube. The few large tissue pieces are dispersed further by passage through a 22-gauge needle. The cell suspensions are decanted to another tube and centrifuged at low speed, and the cells are washed 3 times with PBS. Cell counts are determined for each preparation and adjusted to $10^6$ cells/milliliter.

For each test, $10^5$ cells are incubated with 10% goat preimmune serum for 1 hr and washed 3 times with PBS containing 1% bovine serum albumin. Cells are incubated for 30 min at 37° with supernatant fluid from the hybridoma cultures or ascites fluid diluted 1:5000 in PBS. Control cells are incubated with MPR-1 IgM monoclonal antibody or supernatant fluid from an NS1 culture. After 3 washes with PBS, 60,000 cpm of $^{125}$I-labeled goat anti-mouse immunoglobulin (New England Nuclear) are added, and incubation is done for 30 min at 37°. Unbound iodinated antibody is removed by washing the cells three times with PBS. Scintillation fluid is added to the cells, and the suspensions are transferred to vials for counting in a Packard alpha-counter.

SM1 antibody is strongly reactive with the surface membrane of SCC cell lines and fresh SCC tumors. SM1 antibody is reactive with SCC lung tumors and SCC metastasis to the liver but not to normal tissues including bronchial epithelium, lung parenchyma, liver, kidney and brain. Human red cells and bone marrow cells are also unreactive. SM1 antibody does not react with non-SCC lung tumors, e.g. carcinoid tumor; neuroblastoma; adrenal carcinoma; melanoma; or bronchial carcinoid.

The antigen recognized by SM1 antibody is analyzed by polyacrylamide gel electrophoresis and immunoblotting. Exponentially growing OH-1 cells are washed 3 times with cold PBS and resuspended in PBS with 1 mM phenylmethylsulfonyl fluoride. The cells are lysed in a Potter-Elvehjem homogenizer in ice. The suspension is centrifuged at 600×g to pellet the nuclei and clumped cellular material. The supernatant is centrifuged at 100,000×g for 20 min to pellet the membranes. The pellet is resuspended in 100 microliters of wash buffer and 50 microliters of buffer containing 0.0625 M Tris-HCl (pH 8.6), 10% glycerol, 5% 2-ME, 3% sodium dodecyl sulfate, and 0.0001% bromophenol blue. The sample is analyzed by one-dimensional polyacrylamide gel electrophoresis. The proteins are transferred to nitrocellulose paper using a Hoefer instruments transblot apparatus. The transblot buffer contains 25 millimolar Tris-HCl (pH 8.3), 192 millimolar glycine, and 20% methanol. A current of 0.25 amps at 10 volts is applied overnight. After completion of the protein transfer, the nitrocellulose sheet is cut into strips and air dried. The strips are preincubated with 1% normal goat serum for 1 hr at 37°. The strips are then washed with 0.9% NaCl solution over a period of 10 min. SM1 antibody at a dilution of 1:1000 in PBS and 3% bovine serum albumin is incubated with the strips for 2 hr at 4° C. The controls include SM1 antibody incubated with nitrocellulose strips containing CEM leukemia cell proteins and NS1 myeloma culture medium or MPR-1 antibody incubated with nitrocellulose strips containing SCC cell proteins. After incubation with antibody, the strips are washed with gentle agitation in 5 changes of 0.9% NaCl solution for 2 hr at room temperature. Peroxidase-conjugated goat anti-mouse antibody diluted to 1:500 in 0.9% NaCl solution and 1% bovine serum albumin is added to the strips and incubation is continued for 2 hr at room temperature. To terminate the reaction, the strips are washed with double-distilled water. After drying, the strips are mounted on cardboard for photography.

SM1 antibody recognizes two distinct antigenic determinants on the surface of SCC cells. These determinants have molecular weights of, respectively, approximately 25,000 daltons and 50,000 daltons, as determined by observing the reactivity pattern of SM1 antibody with membrane extract of SCC cells in immunoblots. In contrast, SM1 antibody reacts with none of the antigenic determinants in membrane extract of CEM lymphoblastic leukemia cells.

Immunofluorescence staining of intact SCC cells with SM1 antibody shows that the SM1-recognized antigenic determinants are evenly distributed in a ring pattern around the cell membrane in close to 100% of SCC cells in culture. Immunofluorescence studies on SCC cells show that the SM1 antigen is not sensitive to trypsin or neuraminidase treatment.

Use

Identification of SCC Cells

The monoclonal antibody of the invention can be used to classify lung tumors histologically, according to the following procedure. A cell sample suspected of containing SCC cells is contacted with the antibody, and immune complexes are detected as an indication of the presence of SCC cells. Fresh SCC tumor cells, reacted with SM1 antibody and stained by indirect immunofluorescence using fluorescein-conjugated goat anti-mouse antibody, show fluorescence in a ring pattern at the cell border. Bronchial epithelial cells and bronchial fibroblasts from the same patient do not stain with the antibody. SM1 antibody is useful in distinguishing SCC from non-SCC lung tumors, since non-SCC tumors are unreactive with antibody.

The ability of SM1 to distinguish between SCC and non-SCC lung tumors is of great importance in terms of treatment. Some carcinoid lung tumors are extremely difficult to distinguish from SCC using conventional histological methods, and since the treatment for SCC and carcinoid tumor are radically different, misdiagnosis can have grave consequences. SM1 provides the necessary correct diagnosis, and thus ensures that the correct treatment is administered.

Metastatic SCC cells are easily detected, using SM1, among normal bone marrow cells, as follows. Bone marrow (5-10 cc) is aspirated in a syringe containing 5000 units of preservative-free Heparin. The marrow is diluted with twice the volume of serum-free medium and centrifuged at 800 rpm for 10 minutes in order to isolate the mononuclear cells and tumor cells. The pellet is resuspended in 5 cc of ammonium chloride (i.e., an aqueous solution of 4.145 g $NH_4Cl$, 0.5 g $KHCO_3$, 0.0186 g EDTA made up to 500 ml and having a pH of 7.27), and kept at 4° C. for 3 minutes. 10 cc of serum-free medium is added and the cell suspension is centrifuged at 800 rpm for 5 minutes. If the pellet contains red blood cells the resuspension in $NH_4Cl$ and spin down is repeated. Because $NH_4Cl$ can be toxic to tumor cells, the $NH_4Cl$ treatment is carried out a maximum of three times. The pellet is then washed twice in serum-free medium and cell concentration is adjusted for immunofluorescence (to $10^5$ cells/sample) and flow cytometric analysis (to $10^6$ cells/sample). 100 microliters of a 1:1000 dilution of SM1 antibody is added to each sample and the cells are incubated at 37° C. for 1 hour with vortexing every 15 minutes. The cells are washed twice in serum-free medium and labeled with 30 microliters of a 1:20 dilution of fluorescenated Goat anti-Mouse IgM. The cells are incubated for 1 hour and washed twice in serum-free medium. Samples to be analyzed by flow cytometry are filtered through a four micron cloth mesh to remove any clotted protein; cells analyzed by immunofluorescence are placed on a slide using the wet mount technique. The cells that are highly reactive with SM1 antibody are collected by cell sorting and confirmed to be SCC cells by cytologic examination and growth in methocel.

The SM1 antibody can also be used to detect SCC cells, or cell-free antigen, in plasma and other body fluids, both in vivo and in vitro. For in vivo detection of SCC cells, SM1 antibody can be radiolabeled, using conventional techniques and, in conjunction with conventional in vivo imaging techniques to detect labeled immune complexes, the labeled antibody can be administered in a patient and used to identify tumor sites in the patient. The antibody can also be used to measure the amount of cell-free antigen in a clinical sample, for early detection of disease, or for monitoring tumor bulk.

Therapy

The SM1 antibody can be used therapeutically to kill SCC cells, primary or metastatic, of a patient suffering from SCC. SM1 can be used (with complement) to lyse tumor cells in vitro, or can be used in vivo, alone or coupled to a cytotoxic agent, for the lysis of tumor cells in a patient. The ability of SM1 to lyse cells in the presence of complement is a function of its being of the IgM isotype; generally IgM and IgG2 antibodies are more likely to possess this property. Such lytic antibodies which possess the SCC specificity of SM1 would, therefore, also be useful in therapy in the absence of cytotoxic agents.

Antibody plus complement is used to treat bone marrow which has been removed from a patient, to rid the marrow of metastatic SCC cells prior to re-infusing the cleansed bone marrow into the patient. Such treatment of bone marrow produces over 99% lysis of metastatic SCC cells. The kill rate can be increased even more by employing antibody to which has been coupled, using conventional techniques, a cytotoxic agent such as ricin or adiamycin.

The antibody can also be used for in vivo treatment of SCC, both primary and metastatic. As in the case of in vitro treatment, the antibody can be administered alone (humans have their own complement), or coupled to a cytotoxic agent; an effective amount of the antibody is administered by injection, in combination with a conventional pharmaceutically acceptable carrier substance.

For in vivo use, it will in many instances be preferable to use the Fab portion of the antibody coupled to a cytotoxic agent, rather than the entire antibody, to permit penetration of tumor. Fab cannot be used alone, without a cytotoxic agent, because although it will retain its SCC specificity, its ability to lyse SCC cells will be lost without the Fc portion.

Cytotoxicity of the SM1 antibody toward SCC tumor cells is demonstrated by the chromium release assay. SCC cells are washed 3 times in serum-free medium and labeled with 200 microcuries/milliliter of $Na_3{}^{51}Cr$ for 45 minutes at 37° C. The cells are washed with washing buffer (RPMI 1640, 1 millimole glutamine, 4 millimoles HEPES, and 5% heat inactivated human serum) and allowed to sit on ice for 30 minutes to permit non-absorbed chromium to diffuse from the cell membrane. The cells are washed twice in washing buffer, and the cell concentration is adjusted to $1 \times 10^6$ cells/milliliter. Each test sample contains 450 microliters of cell suspension. 50 microliters of a 1:10 dilution of SM1 antibody in medium is added to each test sample, and the cells are incubated at 37° C. for 30 min. Rabbit complement, at a final concentration of 1:15, is added to each test sample and incubated for an additional 30 minutes, and the cells are washed twice in washing buffer. For multiple antibody treatments the SM1-complement-wash steps can be repeated. After the final treatment, cells are washed three times in washing buffer and the amount of radiolabeled chromium associated with each pellet is determined by a gamma counter, SM1 antibody in the presence of complement lyses greater than 95% of tumor cells at dilutions of 1:10,000 or greater. SM1 antibody at a concentration of 1:100, in the presence of complement at a concentration of 1:10, lyses only about 10% of normal marrow cells while lysing greater than 98% of SCC tumor cells.

Other embodiments are within the following claims.

For example, the antibody can be labeled in a variety of ways, e.g. with fluorine-containing ligands, heavy metals, or $^{13}C$-containing compounds.

I claim:

1. A monoclonal antibody which strongly binds to small cell carcinoma cells compared to the binding of said monoclonal antibody to human neuroblastoma cells, human squamus cell carcinoma cells, and human large-cell undifferentiated lung carcinoma cells, in a radioimmunoassay in which said cells are incubated with said monoclonal antibody and a radiolabeled second antibody capable of binding to said monoclonal antibody, said antibody recognizing an approximately 50,000 dalton antigenic determinant on the surface of small cell carcinoma cells.

2. The antibody of claim 1, wherein said antibody is of the IgM or IgG2 isotype.

3. The antibody of claim 1, wherein said antibody recognizes an approximately 25,000 dalton antigenic determinant on the surface of small cell carcinoma cells.

4. The antibody of claim 1, wherein said antibody is coupled to a cytotoxic agent.

5. The antibody of claim 1, wherein said antibody is labeled with a detectable label.

6. The antibody of claim 5, wherein said antibody is radiolabeled.

7. The antibody of claim 5, wherein said antibody is fluorescently labeled.

8. The antibody of claim 1, wherein said antibody is capable, in the presence of complement, of lysing small cell carcinoma cells in vitro.

9. The monoclonal antibody produced by the hybridoma cell given ATCC Accession No. HB8462.

10. A hybridoma cell capable of producing a monoclonal antibody having the immunological identifying characteristics of the monoclonal antibody produced by hybridoma cell line ATCC Accession No. HB8462.

11. The hybridoma cell given ATTC Accession No. HB8462.

12. A method of detecting the presence of small cell carcinoma cells in a human patient comprising incubating a cell-containing clinical sample from said patient with a monoclonal antibody having the immunological identifying characteristics of the monoclonal antibody produced by hybridoma cell line ATCC Accession No. HB 8462 under conditions sufficient to permit formation of immune complexes and detecting said immune complexes as an indication of the presence of small cell carcinoma cells.

13. A method of lysing small cell carcinoma cells in a clinical sample comprising incubating said sample with a monoclonal antibody having the immunological identifying characteristic of the monoclonal antibody produced by hybridoma cell line ATCC Accession No. HB8462 in the presence of complement under conditions which permit lysis.

14. A method of lysing small cell carcinoma cells in a clinical sample from a patient comprising incubating said sample with an immunotoxin consisting of (1) a monoclonal antibody having the immunological identifying characteristics of the monoclonal antibody produced by hybridoma cell line ATCC Accession No. HB8462 and (2) covalently bound thereto a cytotoxin; under conditions with permit lysis.

15. A monoclonal antibody which strongly binds to small cell carcinoma cells compared to the binding of said monoclonal antibody to human neuroblastoma cells, human squamus cell carcinoma cells, and human large-cell undifferentiated lung carcinoma cells, in an indirect immunofluorescence assay in which said cells are incubated with said monoclonal antibody and a fluorescein-labeled second antibody capable of binding to said monoclonal antibody, said antibody recognizing an approximately 50,000 dalton antigenic determinant on the surface of small cell carcinoma cells.

* * * * *